US006762185B1

(12) United States Patent
Kahn et al.

(10) Patent No.: US 6,762,185 B1
(45) Date of Patent: Jul. 13, 2004

(54) COMPOUNDS USEFUL FOR TREATMENT OF CANCER, COMPOSITIONS CONTAINING THE SAME, AND METHODS OF THEIR USE

(75) Inventors: Michael Kahn, Kirkland, WA (US); Masakatsu Eguchi, Bellevue, WA (US); Sung Hwan Moon, Suwon-shi (KR); Jae Uk Chung, Suwon-shi (KR); Kwang Won Jeong, Seoul (KR)

(73) Assignee: Choongwae Pharma Corporation, Seoul (KR)

(*) Notice: Subject to any disclaimer, the term of this patent is extended or adjusted under 35 U.S.C. 154(b) by 0 days.

(21) Appl. No.: 10/087,005

(22) Filed: Mar. 1, 2002

(51) Int. Cl.$^7$ .................. C07D 487/04; A61K 31/4985
(52) U.S. Cl. ....................................... 514/249; 544/279
(58) Field of Search ........................... 544/279; 514/249

(56) References Cited

U.S. PATENT DOCUMENTS

| | | | |
|---|---|---|---|
| 5,440,013 A | 8/1995 | Kahn | 530/317 |
| 5,475,085 A | 12/1995 | Kahn | 530/317 |
| 5,618,914 A | 4/1997 | Kahn | 530/317 |
| 5,670,155 A | 9/1997 | Kahn | 424/208.1 |
| 5,672,681 A | 9/1997 | Kahn | 530/317 |
| 5,693,325 A | 12/1997 | Kahn | 424/188.1 |
| 5,710,245 A | 1/1998 | Kahn | 530/324 |
| 5,840,833 A | 11/1998 | Kahn | 530/300 |
| 5,859,184 A | 1/1999 | Kahn et al. | 530/300 |
| 5,929,237 A | 7/1999 | Kahn | 544/279 |
| 6,013,458 A | 1/2000 | Kahn et al. | 435/7.1 |
| 6,020,331 A | 2/2000 | Kahn | 514/221 |
| 6,117,896 A | 9/2000 | Qabar et al. | 514/384 |
| 6,184,223 B1 * | 2/2001 | Kahn et al. | 514/249 |
| 6,245,764 B1 | 6/2001 | Kahn et al. | 514/248 |
| 6,294,525 B1 | 9/2001 | Stasiak et al. | 514/183 |
| 6,372,744 B1 | 4/2002 | Qabar et al. | 514/248 |
| 6,413,963 B2 | 7/2002 | Kahn et al. | 514/249 |
| 6,440,955 B1 | 8/2002 | Stasiak et al. | 514/183 |
| 6,548,500 B2 | 4/2003 | Kahn et al. | 514/249 |
| 2001/0039274 A1 | 11/2001 | Kahn et al. | 514/221 |
| 2002/0022620 A1 | 2/2002 | Kahn et al. | 514/221 |
| 2002/0065416 A1 | 5/2002 | Stasiak et al. | 544/350 |
| 2002/0068695 A1 | 6/2002 | Scolastico et al. | 514/9 |
| 2003/0021773 A1 | 1/2003 | Moroder et al. | 424/94.1 |
| 2003/0027819 A1 | 2/2003 | Qabar et al. | 514/224.2 |
| 2003/0105103 A1 | 6/2003 | Golebiowski et al. | 514/249 |

FOREIGN PATENT DOCUMENTS

| | | |
|---|---|---|
| WO | WO 94/03494 A1 | 2/1994 |
| WO | WO 01/00210 A1 | 1/2001 |
| WO | WO 01/16135 A2 | 3/2001 |
| WO | WO 03/006447 | 1/2003 |

OTHER PUBLICATIONS

Simone, Oncology: Introduction, Cecil Textbook of Medicine, 20th Edition, vol. 1, 1004–10, 1996.*
Bejsovec, PubMed Abstract (Curr. Biol. 9(18):R684–7), Sep. 1999.*
Arango, D., et al., Cancer Research, 61: 4910–4915 (2001).
B. Ribinfeld, et al., Science, 272: 1023 (1996).
Behrens, et al., Nature, 382: 638–642 (1996).
Bubinfeld, et al., Science, 275: 1790–1792 (1997).
Cardigan and Nusse, Genes Dev., 11: 3286–3305 (1997).
Casa, et al., Cell. Growth Differ., 10:369–376 (1999).
Chrivia, et al., Nature, 365: 855–859 (1993).
Crawford, et al., Oncogene, 18: 2883–2891 (1999).
Eckner, et al., Genes. Dev., 8: 869–884 (1994).
Gat, et al., Cell, 95: 605–614 (1998).
Hayashi, et al., Proc. Natl. Sci. USA, 94: 242–247 (1997).
He, et al., Science, 281: 1509–1512 (1998).
He, et al., Cell 99: 335–345 (1999).
Hecht, et al., EMBO J. 19:(8) 1839–1850 (2000).
Hsu, et al., Mol. Cell. Biol., 18: 4807–4818 (1998).
Janknecht and Hunter, Nature, 383: 22–23 (1996).
Ken–Ichi Takemaru and Randall T. Moon, J. Cell. Biol., 149:(2) 249–254 (2000).
Kinzler and Vogelstein, Cell, 87: 159–170 (1996).
Kolligs, et al., Mol. Cell. Biol., 19: 5696–5706 (1999).
Miller, et al., Oncogene, 18: 7860–7872 (1999).
Molenaar, et l., Cell 86: 391–399 (1996).
Moon, et al., Trends Genet., 13: 157–162 (1997).
Morin, et al. Science, 275: 1787–1790 (1997).
Moris, et al., Proc. Natl. Acad. Sci. USA, 93: 7950–7954 (1996).
Nuse and Varmus, Cell 69: 1073–1087 (1992).
Orford, et al., J. Cell. Biol., 146: 855–868 (1999).
Polakis, Genes. Dev., 14: 1837–1851 (2000).
Preifer and Polakis, Science, 287: 1606–1609 (2000).
Roose, et al., Science, 285: 1923–1926 (1999).
Sakanaka and William, J. Biol. Chem 274: 14090–14093 (1999).
Sakanaka, et al., Proc. Natl. Acad. Sci. USA, 95: 3020–3023 (1998).
Shaoqiong Chen, et al., J. Cell. Biol., 152:(1) 87–96 (2001).
Shikama, et al., Trends. Cell. Biol., 7: 230–236 (1997).
Shtutman, et al., Proc. Natl. Acad. Sci. USA, 11: 5522–5527 (1999).
Stein, et al., J. Viol., 64:4421–4427 (1990).
Strovel and Sussman, Exp. Cell. Res., 253: 637–648 (1999).
Su, et al., Science, 262: 1734–1737 (1993).
Tao Zhang, et al., Cancer Research, 62: 8664–8667 (2001).
Tetsu and McCormick, Nature, 398: 422–426 (1999).
Tong, D., et al., Oral Oncology 36: 236–241 (2000).
Yost, et al., Genes Dev., 10: 1443–1454 (1996).
Cheguillaume, A. et al., "New Potential Monomers for Solid Phase Synthesis of Hydrazinopeptoids: the $N^\alpha$–Substituted–$N^\beta$–Protected Hydrazinoglycines and Hydrazonoglycinals," Synlett 2000, No. 3, pp. 331–334, Mar. 2000.

(List continued on next page.)

Primary Examiner—Deepak Rao
(74) Attorney, Agent, or Firm—Seed IP Law Group PLLC (57) ABSTRACT

The invention involves compounds having the general formula (I) as described in the claims and pharmaceutical compositions comprising such compounds. The invention also relates to the use of such compounds for inhibiting or treating disorders modulated by Wnt-signaling pathway, such as cancer, especially colorectal cancer.

21 Claims, 8 Drawing Sheets

OTHER PUBLICATIONS

DasGupta, R. and Fuchs, E., "Multiple roles for activated LEF/TCF transcription complexes during hair follicle development and differentiation," *Development 126*: 4557–4568, 1999.

Dolle, R.E., "Comprehensive Survey of Combinatorial Library Synthesis: 1999," *Journal of Combinatorial Chemistry 2*(5): 383–433, Sep./Oct. 2000.

Dooley and Houghten, "The use of positional scanning synthetic peptide combinatorial libraries for the rapid determination of opioid receptor ligands," *Life Sciences 52*(18): 1509–1517, 1993.

Dooley, C.T. et al., "Acetalins: Opioid receptor antagonists determined through the use of synthetic peptide combinatorial libraries," *Proc. Natl. Acad. Sci. USA 90*: 10811–10815, Nov. 1993.

Dooley, C.T. et al., "An All D–Amino Acid Opioid Peptide with Central Analgesic Activity from a Combinatorial Library," *Science 266*: 2019–2022, Dec. 23, 1994.

Eichler, J. et al., "Cyclic Peptide Template Combinatorial Libraries: Synthesis and Identification of Chymotrypsin Inhibitors," *Peptide Research 7*(6): 300–307, 1994.

Fujimuro, M. et al., "A novel viral mechanism for dysregulation of β–catenin in Kaposi's sarcoma–associated herpesvirus latency," *Nature Medicine 9*(3): 300–306, Mar. 2003.

Gallop, M.A. et al., "Applications of Combinatorial Technologies to Drug Discovery. 1. Background and Peptide Combinatorial Libraries," *Journal of Medicinal Chemistry 37*(9): 1233–1251, Apr. 29, 1994.

Graminski and Lerner, "A Rapid Bioassay for Platelet–Derived Growth Factor β–Receptor Tyrosine Kinase Function," *Bio/Technology 12*: 1008–1011, Oct. 1994.

Hartmann, D., "From Alzheimer's disease to skin tumors: The catenin connection," *Proc. Natl. Acad. Sci. USA 98*(19): 10522–10523, Sep. 11, 2001.

Houghten and Dooley, "The use of synthetic peptide combinatorial libraries for the determination of peptide ligands in radio–receptor assays: opioid peptides," *Bioorganic & Medicinal Chemistry Letters 3*(3): 405–412, 1993.

Houghten, R.A. et al., "Generation and use of synthetic peptide combinatorial libraries for basic research and drug discovery," *Nature 354*: 84–86, Nov. 7, 1991.

Houghten, R.A. et al., "The Use of Synthetic Peptide Combinatorial Libraries for the Identification of Bioactive Peptides," *BioTechniques 13*(3): 412–421, 1992.

Janda, K.D., "Tagged versus untagged libraries: Methods for the generation and screening of combinatorial chemical libraries," *Proc. Natl. Acad. Sci. USA 91*: 10779–10785, Nov. 1994.

Lam, K.S. et al., "A new type of synthetic peptide library for identifying ligand–binding activity," *Nature 354*: 82–84, Nov. 7, 1991.

Mak, B.C. et al., "The Tuberin–Hamartin Complex Negatively Regulates β–Catenin Signaling Activity," *The Journal of Biological Chemistry 278*(8): 5947–5951, Feb. 21, 2003.

Randolph, J.T. et al., "Major Simplifications in Oligosaccharide Syntheses Arising from a Solid–Phase Based Method: An Application to the Synthesis of the Lewis b Antigen." J. Am. Chem. Soc. 117, 5712–19, 1995.

Stewart, John M. and Young Janis D., *Solid Phase Peptide Synthesis*, Pierce Chemical Comp., Rockford, Ill., 1984.

Tumelty, D. et al., "Immobilised, Activated Peptides as Reagents for Cyclic and Derivatised Peptide Libraries," *J. Chem. Soc. Chem. Commun.*, pp. 1067–1068, 1994.

Zaloom and Roberts, "Preparation of Azido Derivatives from Amino Acids and Peptides by Diazo Transfer," *J. Org. Chem. 46*: 5173–5176, 1981.

* cited by examiner

COMPOUNDS USEFUL FOR TREATMENT OF CANCER, COMPOSITIONS CONTAINING THE SAME, AND METHODS OF THEIR USE

TECHNICAL FIELD

This invention is related to the filed of cancer treatment and therapeutics. More particularly, it relates to compounds and pharmaceutical compositions containing thereof for treating disorders including cancers which are associated with Wnt signaling pathway. It further relates to methods for treating disorders including cancer which are associated with Wnt signaling pathway.

BACKGROUND OF THE INVENTION

Wnt signaling pathway regulates a variety of processes including cell growth, oncogenesis, and development (Moon et al., 1997, Trends Genet. 13, 157–162: Miller et al., 1999, Oncogene 18, 7860–7872: Nusse and Varmus, 1992, Cell 69, 1073–1087: Cadigan and Nusse, 1997, Genes Dev. 11, 3286–3305: Peifer and Polakis, 2000 Science 287, 1606–1609: Polakis 2000, Genes Dev. 14, 1837–1851). Wnt signaling pathway has been intensely studied in a variety of organisms. The activation of TCF4/β-catenin mediated transcription by Wnt signal transduction has been found to play a key role in its biological functions (Molenaar et al., 1996, Cell 86, 391–399: Gat et al., 1998 Cell 95, 605–614: Orford et al., 1999 J. Cell. Biol. 146, 855–868).

In the absence of Wnt signals, tumor suppressor gene adenomatous polyposis coli (APC) simultaneously interacts with the serine kinase glycogen synthase kinase (GSK)-3β and β-catenin (Su et al., 1993, Science 262, 1734–1737: Yost et al., 1996 Genes Dev. 10, 1443–1454: Hayashi et al., 1997, Proc. Natl. Acad. Sci. USA, 94, 242–247: Sakanaka et al., 1998, Proc. Natl. Acad. Sci. USA, 95, 3020–3023: Sakanaka and William, 1999, J. Biol. Chem 274, 14090–14093). Phosphorylation of APC by GSK-3β regulates the interaction of APC with β-catenin, which in turn may regulate the signaling function of β-catenin (B. Rubinfeld et al., Science 272, 1023, 1996). Wnt signaling stabilizes β-catenin allowing its translocation to the nucleus where it interacts with members of the lymphoid enhancer factor (LEF1)/T-cell factor (TCF4) family of transcription factors (Behrens et al., 1996 Nature 382, 638–642: Hsu et al., 1998, Mol. Cell. Biol. 18, 4807–4818: Roose et all., 1999 Science 285, 1923–1926).

Recently c-myc, a known oncogene, was shown to be a target gene for β-catenin/TCF4-mediated transcription (He et al., 1998 Science 281 1509–1512: Kolligs et al., 1999 Mol. Cell. Biol. 19, 5696–5706). Many other important genes, including cyclin D1, and metalloproteinase, which are also involved in oncogenesis, have been identified to be regulated by TCF4/bata-catenin transcriptional pathway (Crawford et al., 1999, Oncogene 18, 2883–2891: Shtutman et al., 1999, Proc. Natl. Acad. Sci. USA., 11, 5522–5527: Tetsu and McCormick, 1999 Nature, 398, 422–426).

Moreover, overexpression of several downstream mediators of Wnt signaling has been found to regulate apoptosis (Moris et al., 1996, Proc. Natl. Acad. Sci. USA, 93, 7950–7954: He et al., 1999, Cell 99, 335–345: Orford et al., 1999 J. Cell. Biol., 146, 855–868: Strovel and Sussman, 1999, Exp. Cell. Res., 253, 637–648). Overexpression of APC in human colorectal cancer cells induced apoptosis (Moris et al., 1996, Proc. Natl. Acad. Sci. USA., 93, 7950–7954), ectopic expression of β-catenin inhibited apoptosis associated with loss of attachment to extracellular matrix (Orford et al, 1999, J. Cell Biol.146, 855–868). Inhibition of TCF4/β-catenin transcription by expression of dominant-negative mutant of TCF4 blocked Wnt-1-mediated cell survival and rendered cells sensitive to apoptotic stimuli such as anti-cancer agent (Shaoqiong Chen et al., 2001, J. Cell. Biol., 152, 1, 87–96) and APC mutation inhibits apoptosis by allowing constitutive survivin expression, a well-known anti-apoptotic protein (Tao Zhang et al., 2001, Cancer Research, 62, 8664–8667).

Although mutations in the Wnt gene have not been found in human cancer, a mutation in APC or β-catenin, as is the case in the majority of colorectal tumors, results in inappropriate activation of TCF4, overexpression of c-myc and production of neoplastic growth (Bubinfeld et al, 1997, Science, 275, 1790–1792: Morin et al, 1997, Science, 275, 1787–1790: Casa et al, 1999, Cell. Growth. Differ. 10, 369–376). The tumor suppressor gene (APC) is lost or inactivated in 85% of colorectal cancers and in a variety of other cancers as well (Kinzler and Vogelstein, 1996, Cell 87, 159–170). APC's principal role is that of a negative regulator of the Wnt signal transduction cascade. A center feature of this pathway involves the modulation of the stability and localization of a cytosolic pool of β-catenin by interaction with a large Axin-based complex that includes APC. This interaction results in phosphorylation of β-catenin thereby targeting it for degradation.

CREB binding proteins (CBP)/p300 were identified initially in protein interaction assays, first through its association with the transcription factor CREB (Chrivia et al, 1993, Nature, 365, 855–859) and later through its interaction with the adenoviral-transforming protein E1A (Stein et al., 1990, J. Viol., 64, 4421–4427: Eckner et al., 1994, Genes. Dev., 8, 869–884). CBP had a potential to participate in variety of cellular functions including transcriptional coactivator function (Shikama et al., 1997, Trends. Cell. Biol., 7, 230–236: Janknecht and Hunter, 1996, Nature, 383, 22–23). CBP/p300 potentiates β-catenin-mediated activation of the siamois promoter, a known Wnt target (Hecht et al, 2000, EMBO J. 19, 8, 1839–1850). β-catenin interacts directly with the CREB-binding domain of CBP and β-catenin synergizes with CBP to stimulate the transcriptional activation of TCF4/β-catenin (Ken-Ichi Takemaru and Randall T. Moon, 2000 J. Cell. Biol., 149, 2, 249–254).

From this background, TCF4/β-catenin and CBP complex of Wnt pathway can be taken as target molecules for the regulation of cell growth, oncogenesis and apoptosis of cells, etc. That is, there is a need for compounds that block TCF4/β-catenin transcriptional pathway by inhibiting CBP, and therefore can be used for treatment of cancer, especially colorectal cancer.

SUMMARY OF THE INVENTION

It is an object of the present invention to provide a compound having general formula (I) as follows:

wherein, $R_1$ is a bicyclic aryl group having 8 to 11 ring members, which may have 1 to 3 heteroatoms selected from nitrogen, oxygen or sulfur, and $R_2$ is a monocyclic aryl group having 5 to 7 ring members, which may have 1 to 2 heteroatoms selected from nitrogen, oxygen or sulfur, and aryl ring in the compound may have one or more substituents selected from a group consisting of halide, hydroxy, cyano, lower alkyl, and lower alkoxy group.

It is an object of the present invention to provide a pharmaceutical composition comprising a safe and effective amount of the compound having general formula (I) and pharmaceutically acceptable carrier, which can be used for treatment of disorders modulated by Wnt signaling pathway, especially by TCF4-β-catenin-CBP complex.

It is an object of the present invention to provide a method for inhibiting the growth of tumor cells by using the above-described composition of the present invention.

It is an object of the invention to provide a method for inducing apoptosis of tumor cells by using the above-described composition of the present invention.

It is an object of the invention to provide a method for treating a disorder modulated by TCF4-β catenin-CBP complex by using the above-described composition of the present invention.

It is an object of the present invention to provide a method of treating cancer such as colorectal cancer by administering the composition of the present invention together with other anti-cancer agent such as 5-fluorouracil (5-FU).

BRIEF DESCRIPTION OF THE DRAWING

The compound having general formula (I) wherein $R_1$ is 2-naphthyl and $R_2$ is phenyl is used for this experiment (it is referred to as 'TCF4 compound' hereinafter). Each transfection was performed in duplicate and repeated at least three times. SW480 cells were transfected transiently with 4.0 μg firefly luciferase reporter plasmid (pTOPFlash) and 0.8 μg renilla luciferase reporter plasmid (pRL-null). Firefly luciferase activity was normalized to renilla luciferase activity.

FIG. 3. Specific binding of TCF4 compound to CBP. SW480 cells were transiently transfected with β-catenin or CBP expression plasmid. 48 hours after transfection, nuclear protein extracts were collected. 14C-Tcf4 was incubated with nuclear lysate.

FIG. 5A. Surviving mRNA (363 bp) level was assessed by RT-PCR in SW480 cell 24 hours after incubation 25 μM TCF4 compound. β-actin mRNA (564 bp) level is shown as an internal control. FIG. 5B. Survivin protein (MW 16,500) level was assessed by Western blots in SW480 using anti-survivin monoclonal antibody after TCF4 incubation with compound for 48 hrs.

FIG. 6. TCF4 compound induces caspase-3 activation in a dose-dependent manner. SW480 cells were treated with TCF4 compound for 24 hours. Whole cell protein extracts were prepared and 100 μg aliquots of protein extracts were incubated with Cbz-DEVD-R110 substrate for 2 hours at 37° C. Relative fluorescence unit (RFU) was obtained by subtracting the unit values of the blank control from the experimental measured values.

FIG. 7. Cell growth and colony formation assays. SW480 cells were treated with TCF4 compound. The resulting cells are placed in a soft agar plate and incubated at 37° C. in $CO_2$ incubator for 8 days. Number of colonies were counted under microscope.

DETAILED DESCRIPTION OF THE INVENTION

The present invention relates to a compound having the following general formula (I):

wherein, $R_1$ is a bicyclic aryl group having 8 to 11 ring members, which may have 1 to 3 heteroatoms selected from nitrogen, oxygen or sulfur, and $R_2$ is a monocyclic aryl group having 5 to 7 ring members, which may have 1 to 2 heteroatoms selected from nitrogen, oxygen or sulfur. Preferably, $R_1$ is naphthyl, quinolinyl or isoquinolinyl group, and $R_2$ is phenyl, pyridyl or piperidyl. More preferably, $R_1$ is naphthyl, and $R_2$ is phenyl.

In the context of the present invention, said aryl groups in the compound having general formula (I) may be further substituted by one or more substituents, for example, selected from a group consisting of halide, hydroxy, cyano, lower alkyl, and lower alkoxy group.

In a preferred embodiment of the present invention, the compound of the present invention has a (6S,10R)-configuration as follows:

wherein $R_1$ and $R_2$ have the same meanings as defined above.

In a more preferred embodiment of the present invention, the compound of general formula (I) has the following chemical structure wherein R₁ is naphthyl and R₂ is phenyl, which is named as 'TCF4 compound' in the present detailed description.

Compounds having general formula (I) can be prepared from the disclosure of U.S. Pat. No. 6,184,223 assigned to Molecumetics Ltd. References cited therein are also taken into the consideration to accomplish the present invention. According to the disclosure of said patented invention, the compounds having general formula (I) could mimic the secondary structure of reverse-turn regions of biologically active peptide and proteins. Such reverse-turn mimetics are known to have utility in the treatment of cell adhesion-indicated diseases, such as multiple sclerosis, atherosclerosis, asthma and inflammatory bowel disease. In the examples of U.S. Pat. No. 6,184,223, the reverse-turn mimetics having similar structure with the compounds having general formula (I) are shown to have an antagonistic effect to opiate receptors. Further, potential analgesic activity us shown for a series of the compounds.

However, the inventors of the present invention surprisingly found that the compounds having general formula (I) have an anti-cancer activity toward cancer cells, by regulating Wnt signaling pathway in cells. Especially, the compounds having above-described general formula (I) are found to be useful for the treatment of colorectal cancer. The inventors of the present invention further found that, when the compound having general formula (I) has a stereospecificity of (6S,10R) configuration, its anti-cancer effect is especially higher than those of other configurations. For example, the above-described 'TCF compound' is proven to be especially effective for inhibiting cancer cells, i.e., SW480 cells.

It is found in the present invention that the compound of general formula (I) can inhibit CBP-mediated transcriptional activation in cancer cells by specifically binding to CBP, and it is supported by immunoprecipitation of CBP of SW480 cells with the compound of the present invention. Compound of the present invention also inhibits survivin expression in SW480 cells, and therefore inhibits oncogenic activity in cancer cells. Thus, the compound of the present invention can be used for inhibiting cancer cells, and thus would be useful for the regulation of cell growth. Supporting such results, compound of the present invention further shows that it can induce caspase-3 activation in SW480 cells, and therefore inducing the apoptotic activity in cells. Thus, the compound of the present invention can be also advantageously used for inducing apoptosis in cells.

In another aspect of the present invention, a pharmaceutical composition containing the compound having the general formula (I) is disclosed. For the preparation of the pharmaceutical composition containing the present compounds, a skilled person in the art can use publicly known knowledge and techniques which are known in the pertinent art. Generally known varieties of carriers and other additives are used for the preparation of the composition of the present invention. The composition containing the compound of general formula (I) can be used for treatment of disorders modulated by Wnt signaling pathway, especially cancer, more especially colorectal cancer.

In another aspect of the present invention, a method for inhibiting the growth of tumor cell in a subject in which the method comprises administering to a tumor cell a safe and effective amount of the compounds of the present invention is disclosed. The composition containing such compounds also can be used for the inhibition of tumor cells. Thus, this method can be useful to treat cancer in a mammalian subject. It can be advantageously used for treating colorectal cancer.

In another aspect of the present invention, a method for treating a disorder modulated by Wnt signaling pathway in which the method comprises administering to a patient a safe and effective amount of the compounds having general formula (I) is disclosed. Pharmaceutical composition containing the compound of the present invention can be also used for this purpose. In this connection, it is found in the present invention that the compounds having general formula (I) or the pharmaceutical composition containing thereof can be useful for the treatment of disorder modulated by TCF4—β catenin—CBP complex, which is believed to be responsible for initiating the overexpression of cancer cells related to Wnt signaling pathway. Thus, it is another aspect of the present invention to provide a method for the treatment of disorder modulated by TCF4—β catenin—CBP complex, using the compounds having the general formula (I).

Further, because the treatment of cancer is also closely related to inducing apoptosis in cancer cells in a subject, the present invention is also directed to a method of inducing apoptosis in cancer cells using the compounds of general formula (I).

It has been known from previous art that 5-FU [Fluorouracil; 5-fluoro-2,4(1H, 3H)-pyrimidinedione] can induce apoptosis in cultured oral cancer cells (D. Tong et al., Oral Oncology 36, 2000 236–241). Further, it is also known that colon cancer has a sensitivity to 5-FU (D. Arango et al., Cancer Research 61, 2001 4910–4915). In the present invention, therefore, the combination of 5-FU having established anti-cancer activity and the compounds of formula (I) of the present invention is prepared and tested against SW480 cell lines. As a result, it is found that the combination of 5-FU with the compounds of the present invention, especially TCF4 compound, has a remarkable effect for inhibiting cancer cell growth such as SW480 cells. Therefore, it is yet another aspect of the present invention to provide a method of treating cancer, which comprises administering to a subject a safe and effective amounts of the compound having formula (I) of claim 1 together with other anti-cancer agent such as 5-Fu.

The following non-limiting examples illustrate the compound, composition, and methods of use of this invention.

EXAMPLE 1

(1) Preparation of Naphthylmethylamine Acetal Resin

Bromoacetal PS resin 2 g (0.9 mmol/g, 1.8 mmol) was swelled in DMSO 20 mL and 1-Naphthalenemethylamine 5 mL (36 mmol, 20 equiv.) was added to the resin solution. The resulting resin mixture was slowly rotated at 70~80° C. for a day. The resin was cooled down to room temperature, filtered, and washed with DMF. The upper procedure was repeated again. The chloranil test was active.

(2) Preparation of Fmoc-Tyr(OtBu)-naphthylmethylamido Acetal Resin

Naphthylmethylamine acetal resin (2 g; ~1.8 mmol) was swelled in DMF and Fmoc-Tyr(OtBu)-OH 3.306 g (7.2 mmol, 4 equiv), HOAT 0.979 g (7.2 mmol, 4 equiv), DIC 1.13 ml (7.2 mmol, 4 equiv), DIEA 2.5 ml (14.4 mmol, 8 equiv) and DMF 20 mL were mixed and agitated for 20 minutes. The amino acid solution was added to the resin and shaken for 1 day. After this, Chloranil test was slightly active. Thus, additional Fmoc-Tyr(OtBu)-OH 1.24 g (2.7 mmol, 1.5 equiv), HOAT 0.37 g (2.7 mmol, 1.5 equiv), DIC 0.42 ml (2.7 mmol, 1.5 equiv), DIEA 0.94 ml (14.4 mmol, 3 equiv) and DMF 20 mL were mixed and agitated for 20 minutes. The amino acid solution was added to the resin and shaken for 1 day, at which point the chloranil test showed no free secondary amine groups present on the resin. The resin was filtered, rinsed with DMF and DCM and dried in vacuo.

<Fmoc Quantitation>

The known quantity of resin (4.3 mg) was weighed into 15 ml Falcon tube. To the tube were added 0.4 ml of piperidine and 0.4 ml of DCM. The mixture was allowed to cleave for 30 min, at which point MeOH (1.6 ml) and DCM (7.6 ml) were added to bring the total volume to 10 mL. The spectrometer was zeroed with a blank solution containing 0.4 mL of piperidine, 1.6 ml of MeOH, and DCM to make 10 ml. The absorbance was measured at 300 nm and the loading level was 0.506 mmol/g.

(3) Preparation of Fmoc-β-Ala-amido-Tyr(OtBu)-naphthylmethylamido Acetal Resin Fmoc-Tyr(OtBu)-naphthylmethylamido acetal resin (2 g; 1.01 mmol) was swelled in DMF and 25% piperidine 20 mL was added to the resin. The resin solution was shaken for 30 min., filtered and rinsed with DMF. The Additional 25% piperidine was added to the resin and the resin solution was shaken for 30 min., filtered and rinsed with DMF. Kaiser test was active.

The Fmoc-deprotected resin was swelled in DMF and Fmoc-β-Ala-OH 788 mg (2.53 mmol, 2.5 equiv), HOBT 342 mg (2.53 mmol, 2.5 equiv), PyBOP 1.316 g (2.53 mmol, 2.5 equiv), DIEA 0.88 ml (5.06 mmol, 5 equiv) and DMF 25 mL were mixed and agitated for 20 minutes. The amino acid solution was added to the resin and shaken for 1 day. After this, Kaiser test was slightly active. Fmoc-β-Ala-OH 788 mg (2.53 mmol, 2.5 equiv), HOBT 342 mg (2.53 mmol, 2.5 equiv), PyBOP 1.316 g (2.53 mmol, 2.5 equiv), DIEA 0.88 ml (5.06 mmol, 5 equiv) and DMF 25 mL were mixed and agitated for 20 minutes. The amino acid solution was added to the resin and shaken for 1 day, at which point the chloranil test showed no free amine groups present on the resin. The resin was filtered, rinsed with DMF and DCM and dried in vacuo. The loading level was 0.856 mmol/g and measured by Fmoc-quantitation.

(4) Preparation of p-Nitrophenoxycarbonyl-β-Ala-amido-Tyr(OtBu)-naphthylmethylamido Acetal Resin

Fmoc-β-Ala-amido-Tyr(OtBu)-naphthylmethylamido acetal resin (2 g; 1.712 mmol) was swelled in DMF and 25% piperidine 20 mL was added to the resin. The resin solution was shaken for 30 min., filtered and rinsed with DMF. The Additional 25% piperidine was added to the resin and the resin solution was shaken for 30 min., filtered and rinsed with DMF and DCM. Kaiser test was active.

The Fmoc-deprotected resin was swelled in THF/MC 1/1 v/v 20 mL. After 20 min., DIEA 0.89 mL (5.136 mmol, 3 equiv.) was added to the swelled resin and the temperature was cooled down to 5° C. (ice bath). Then p-Nitrophenyl chloroformate 1.035 g (5.136 mmol, 3 equiv.) in THF/MC 1/1 v/v 10 mL was slowly added to the resin solution (exothermic).

After this, the resulting resin solution was shaken for 2 days at room temperature Kaiser test was slightly active, so the upper process was repeated again. The resin solution was shaken for 4 hours, at which point the Kaiser test showed no free amine groups present on the resin.

The resin was rinsed with DCM, DMF and DCM, and dried in vacuum dessicator.

(5) Preparation of Benzylureido-β-Ala-amido-Tyr(OtBu)-naphthylmethylamido Acetal Resin p-Nitrophenoxycarbonyl-β-Ala-amido-Tyr(OtBu)-naphthylmethylamido acetal resin 2 g (1.712 mmol) was swelled in DMF, and Bezylamine 917 mg (8.56 mmol, 5 equiv.) and DIEA 1.5 mL (8.56 mmol, 5 equiv.) in DMF 20 mL were added to the resin. The resin solution was shaken for 1 day, at which point the piperidine test showed no p-Nitrophenyl carbamate groups present on the resin. The resin was rinsed with DMF, DCM and dried in vacuum dessicator.

(6) Preparation of 6-(4-Hydroxy-benzyl)-8-naphthalen-1-ylmethyl-4-oxo-hexahydro-pyrazino[1,2-α]pyrimidine-1-carboxylic Acid Benzylamide 20 mL of formic acid was added to the welled dried resin Benzylureido-β-Ala-amido-Tyr(OtBu)-naphthylmethylamido acetal resin 2 g (1.712 mmol). And the resin solution was slowly rotated for overnight using rotary evaporator. The resin was filtered through sintered glass filter and the filtrate was concentrated in vacuum and lyophilized to remove formic acid residue. The crude cju-0629-49 was purified by column chromatography (MeOH/DCM 95/5 v/v), recrystallized using by EA/n-Hexane and decolored using charcoal to afford pure cju-0629-49 260 mg (0.486 mmol) as a white solid.

Total yield: 27% $R_f$=0.3 (MeOH/DCM 5/95 v/v) $^1$H-NMR (300 MHz, DMSO-$d_6$) δ 2.1 (m, 2H), 3.0~3.2 (m, 4H), 3.55 (t, 1H, J=10.7 Hz), 3.85 (m, 1H), 4.18 (dd, 1H, J=5.4, 15.7 Hz), 4.35 (dd, 1H, J=5.4, 15.7 Hz), 4.90 (d, 1H, J=15.3 Hz), 5.15 (m, 2H), 5.75 (dd, 1H, J=4.1, 10.5 Hz), 6.55 (d, 2H, J=8.5 Hz), 6.90 (d, 2H, J=8.5 Hz), 7.20~7.40 (m, 6H), 7.45~7.60 (m, 4H), 7.95~8.00 (m, 2H), 8.15 (m, 1H), 9.20 (bs, 1H). ESI-MS: M+1 536 HPLC: 99.05%

EXAMPLE 2

Figure 1:
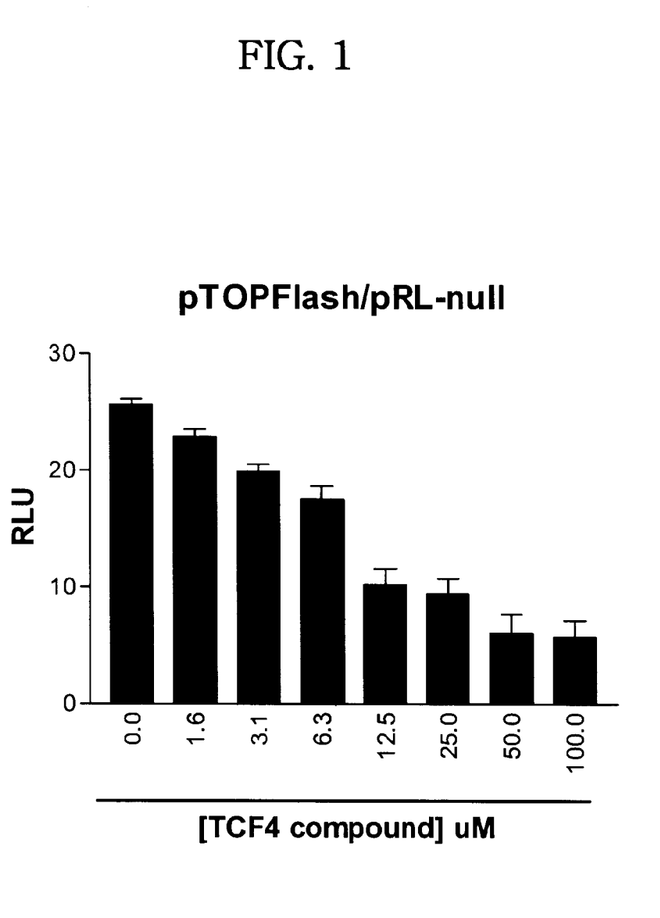
FIG. 1. TCF4 compound inhibits the transcription of the TCF4 responsive reporter gene luciferase in a dose-dependent manner.

Results of the Following Example Shows That TCF4 Compound of the Present Invention Inhibits TCF4/β-catenin Transcriptional Activation Pathway To determine whether or not the present TCF4 compound functionally inhibits TCF4/β-catenin transcriptional pathway, pTOPFlash reporter construct containing three copies of the optimal TCF motif CCTTTGATC upstream of a minimal c-fos promoter driving luciferase expression was used. pRL-null or pRL-CMV(Promega) was used as a control reporter. SW480 cells were maintained in DMEM with 10% fetal bovine serum supplemented with non-essential amino acid and antibiotics. Transient transfections into SW480 cells were carried out by Superfect (Qiagen, 301307). For TCF4/β-catenin reporter gene assay, 4 μg of pTOPFlash and 0.8 μg of pRL-null were cotransfected. After 24 hours of transfection, SW480 cells were treated with TCF4 compound at varying concentrations. Firefly luciferase and renilla luciferase activities were measured 24 hours after said TCF4 compound treatment, and the firefly luciferase activity was normalized to the renilla luciferase activity (FIG. 1).

Figure 2:
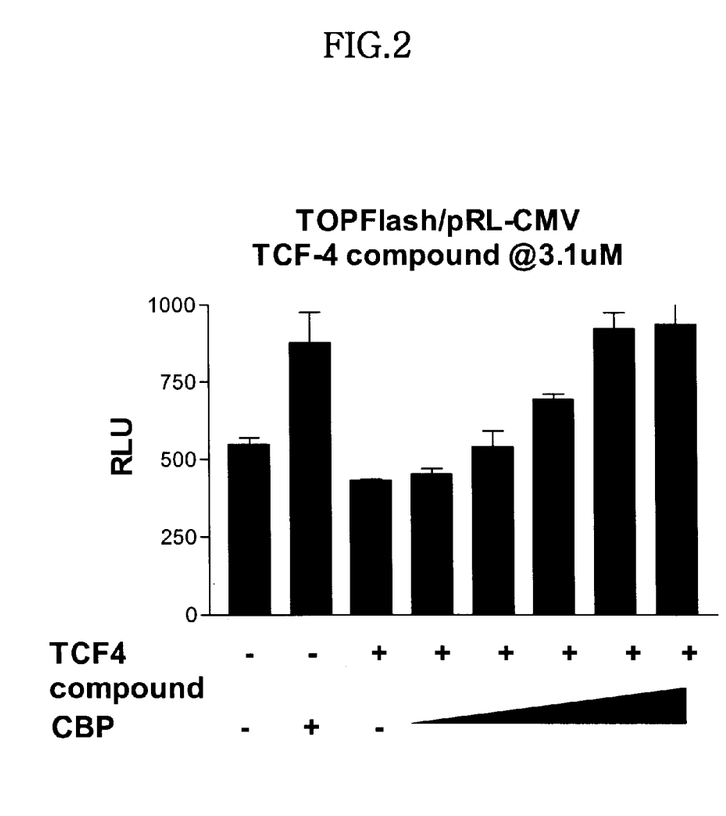
FIG. 2. TCF4 compound inhibits CBP-mediated transcriptional activation. SW480 cells were cotransfected with 1.1 μg of the pTOPFlash reporter, and 0.8 μg pRL-CMV, in the presence or absence of TCF4 compound and CBP and/or β-catenin, which are present in various concentrations(1.1 to 3.3 μg), is shown to reverse the inhibiting action of TCF4 compound on CBP-mediated transcriptional activation.

In order to determine the inhibitory effect of TCF4 compound on CBP-mediated transcriptional activation, reporter plasmid pTOPFlash (1.1 μg), CBP expression vector (1.1 to 3.3 μg), wild type beta-catenin expression vector (1.1 to 3.3 μg) and pRL-null (0.8 μg) were cotransfected into SW480. Total amount of DNA was adjusted to 6.3 μg. After 24 hours incubation, TCF4 compound was added and cells were washed and luciferase activity was measured. Firefly luciferase activity was normalized to renilla luciferase activity (FIG. 2).

EXAMPLE 3

Figure 3:
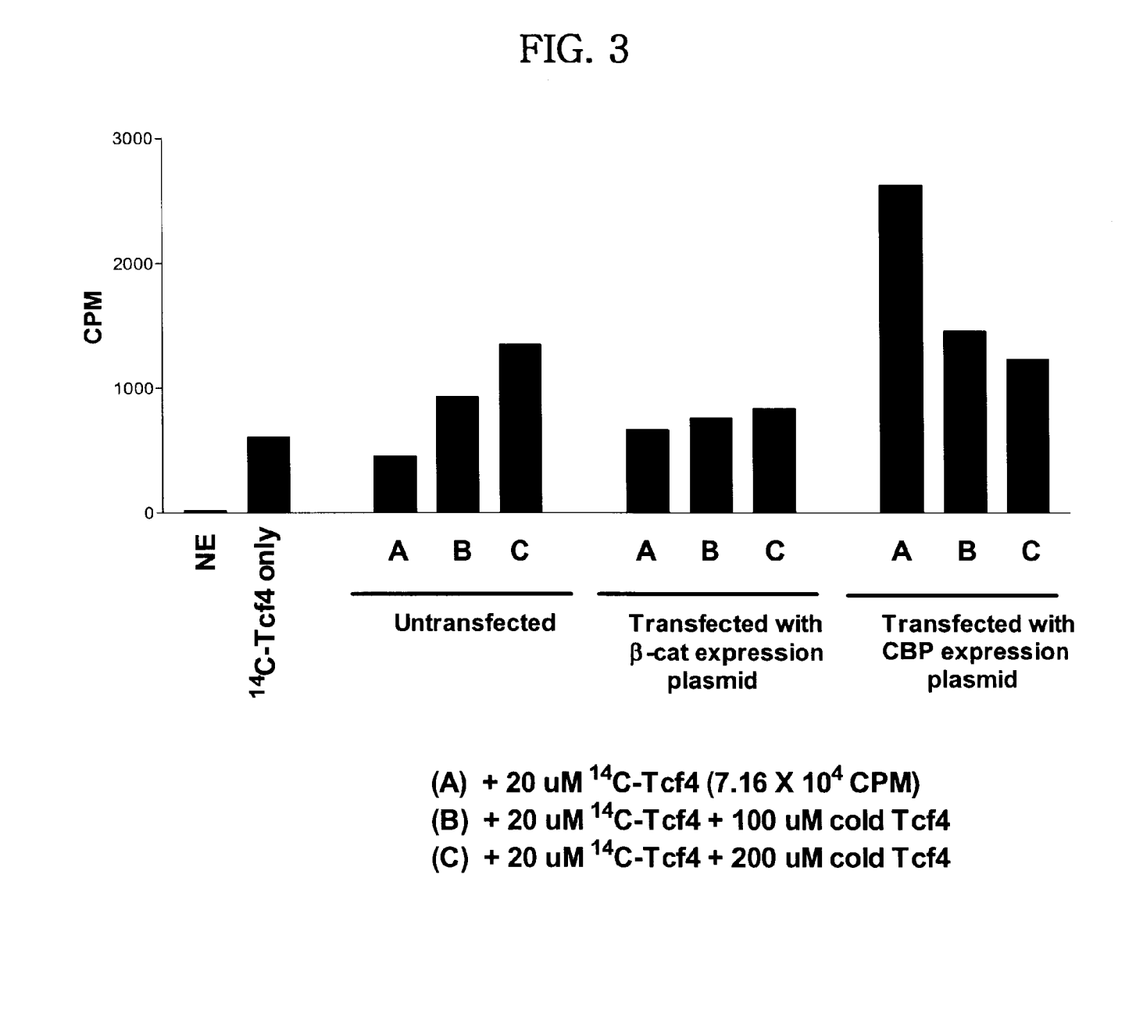

Results of the Following Example Shows Specific Binding of TCF4 Compound to CBP (FIG. 3).

Nuclear protein extracts from SW480 transfected with CBP expression vector or wild type β-catenin expression vector were collected using NE-PER Nuclear and Cytoplasmic Extraction Reagents (Pierce) and incubated with $^{14}$C-TCF4 compound at 4° C. for 18 hours. Each samples were washed with Sephadex G-25 columns equilibrated with 5 mL of PBB (20 mM HEPES, pH 7.9, 60 mM NaCl, 6 mM $MgCl_2$, 0.5 mM EDTA, 0.1% NP-40, 20% glycerol, 5 mM 2-ME, 1 mM PMSF) and protein samples eluted by centrifugation were transferred to a scintillation vial containing 2 mL of scintillation fluid. Radio activities were counted using scintillation counter (Beckman).

EXAMPLE 4

Figure 4:
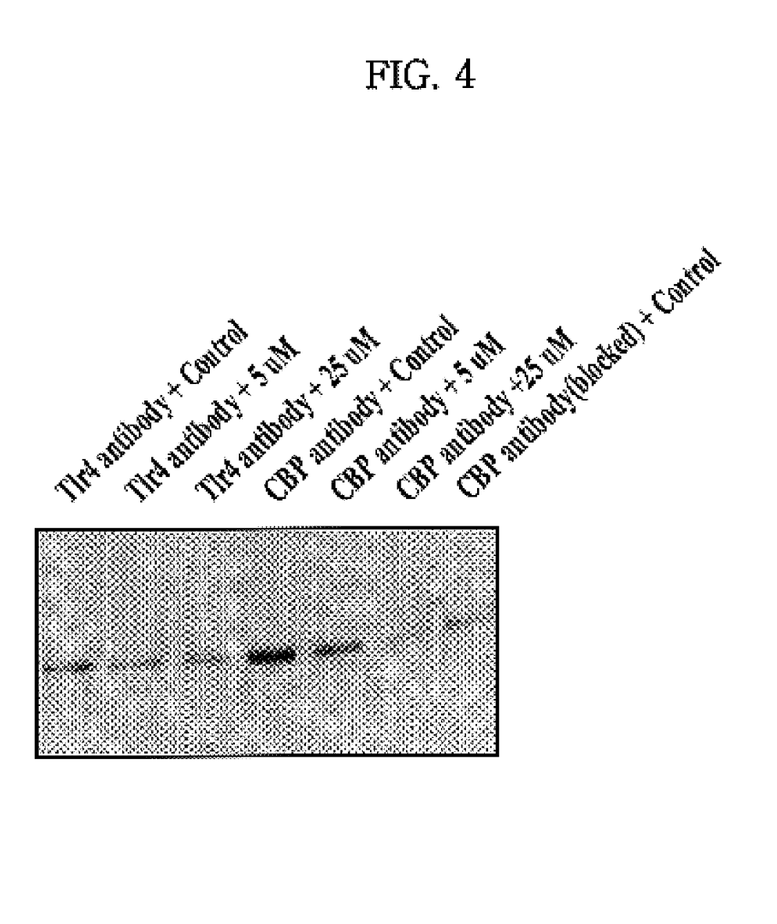
FIG. 4. Co-immunoprecipitation of β-catenin with CBP in nuclear extracts of SW480 cells treated with TCF-4 compound. SW480 cells were treated with TCF4 compound (5 μM, 25 μM) for 24 hours. Nuclear protein extracts were collected and immunoprecipitation was performed using rabbit anti-CBP polyclonal antibody. Unbound protein was washed away and Western blots was performed with mouse anti-β-catenin monoclonal antibody.

Inhibitory Effect of the TCF4 Compound on CBP is Determined by Co-immunoprecipitation of β-catenin with CBP in Nuclear Extracts of SW480 Cells Which are Treated with the TCF4 Compound Specifically SW480 cells were treated with TCF4 compound (5 μm, 25 μM) for 24 hours. Nuclear protein extracts were collected and cleared with buffer containing 20 mM Tris-HCl, pH 8.0, 75 mM NaCl, 1.5 mM $MgCl_2$, 1 mM EGTA, 0.5% NP40, 10% glycerol and protease inhibitor cocktail. 30ul of 50% slurry of protein A agarose was added to the diluted nuclear lysates. After incubation for 1 hour, clear nuclear lysates were collected by centrifugation. Immunoprecipitation was performed using rabbit anti-CBP polyclonal antibody. Rabbit polyclonal Tlr4 antibody was used as a negative control to show that β-catenin and CBP interaction is specific in the present experiments. Unbound protein was washed and Western blot was performed with mouse anti-β-catenin monoclonal antibody (FIG. 4).

EXAMPLE 5

Figure 5:
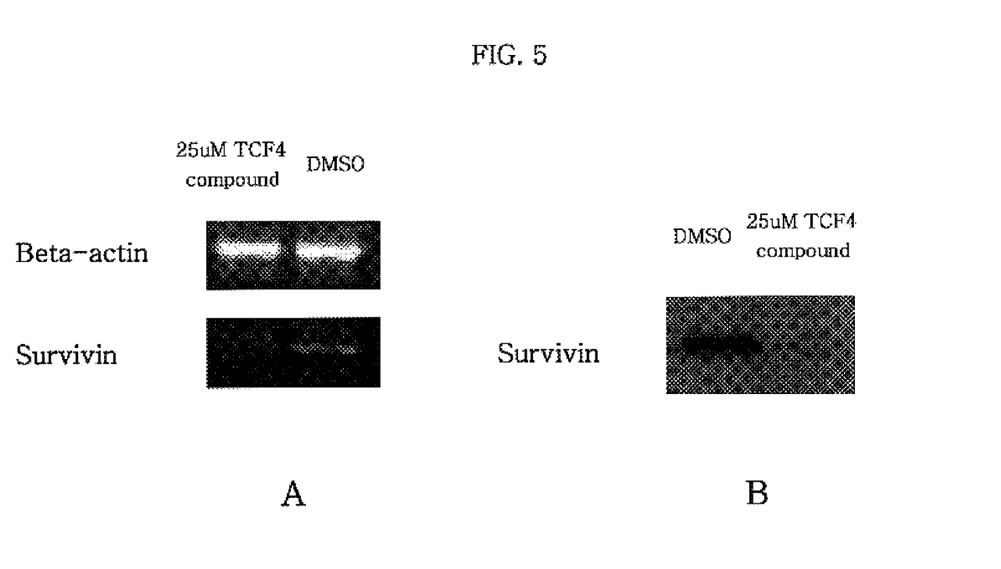
FIGS. 5A and 5B. Inhibition of survivin expression by TCF4 compound in SW486 cells.

This Example Demonstrates that TCF4 Compound Inhibits mRNA and Protein Expression Level of Survivin, Which is One of Anti-apoptotic Proteins Total RNA was isolated from SW480 cells treated with the TCF4 compound using Rneasy midi kit (Qiagen, Valencia, Calif., 75142). One microgram of RNA was used as a template for RT-PCR. The expression of survivin was evaluated with RT-PCR and Western blot. The primer used to detect fragments of the survivin gene was designed from published human sequences (Cancer Res., 2001, 62, 8664–8667). The sequences used were 5'-AGCCCTTTCTCAAGGACCAC-3' and 5'-GCACTTTCTTCGCAGTTTCC-3', which can give an amplified product of 363 bp. The RT-PCR reaction was processed by Access RT-PCR system (Promega A1260). (FIG. 5) Survivin 6E4 Monoclonal antibody (Cell signaling Technology, 2802) was used for Western blot of TCF4 compound treated SW480 cells. (FIG. 5B).

EXAMPLE 6

Figure 6:
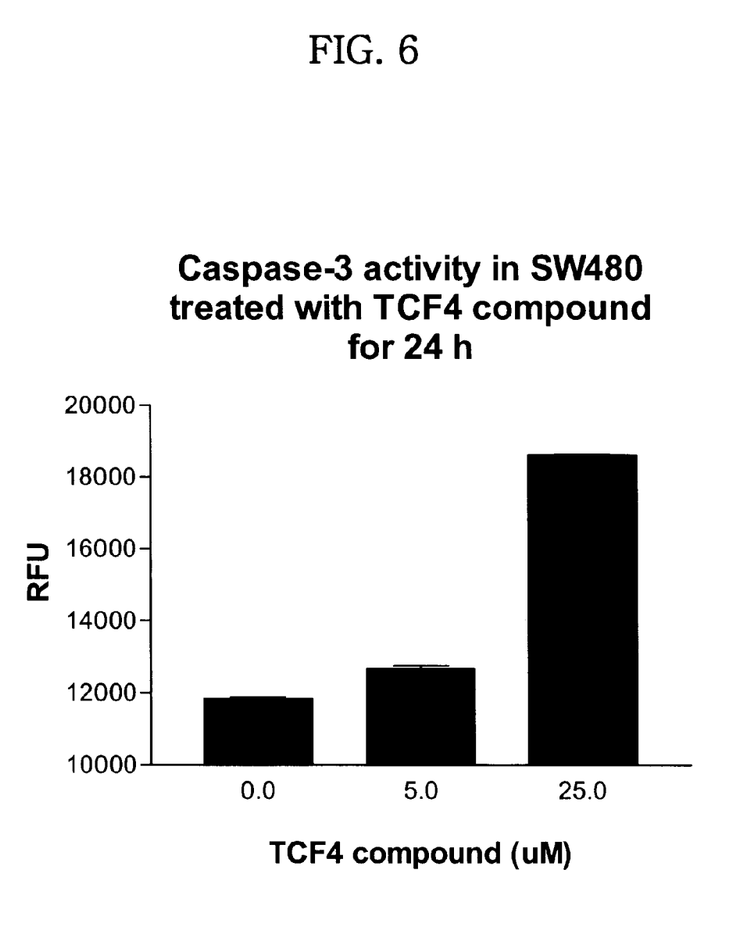

This Example Demonstrates That the TCF4 Compound Induces Apoptosis in SW480 Colon Cancer Cell Line. For this Purpose, Function of an Enzyme Celled Caspase 3 in SW480 Cancer Cell was Followed SW480 cells were treated with TCF4 compound for 24 hours, collected and washed with PBS, and lysed in 100 μl ice cold hypotonic lysis buffer which is commercially available (Promega). 100 μg of the cell extracts were incubated in reaction buffer containing Cbz-DEVD-R110 (caspase-3 substrate: Promega) at 37° C. for 2 hours (FIG. 6). It is clear the FIG. 6 that caspase-3 activity was stimulated by the presence of the TCF4 compound, in a dose dependent manner.

EXAMPLE 7

Figure 7:
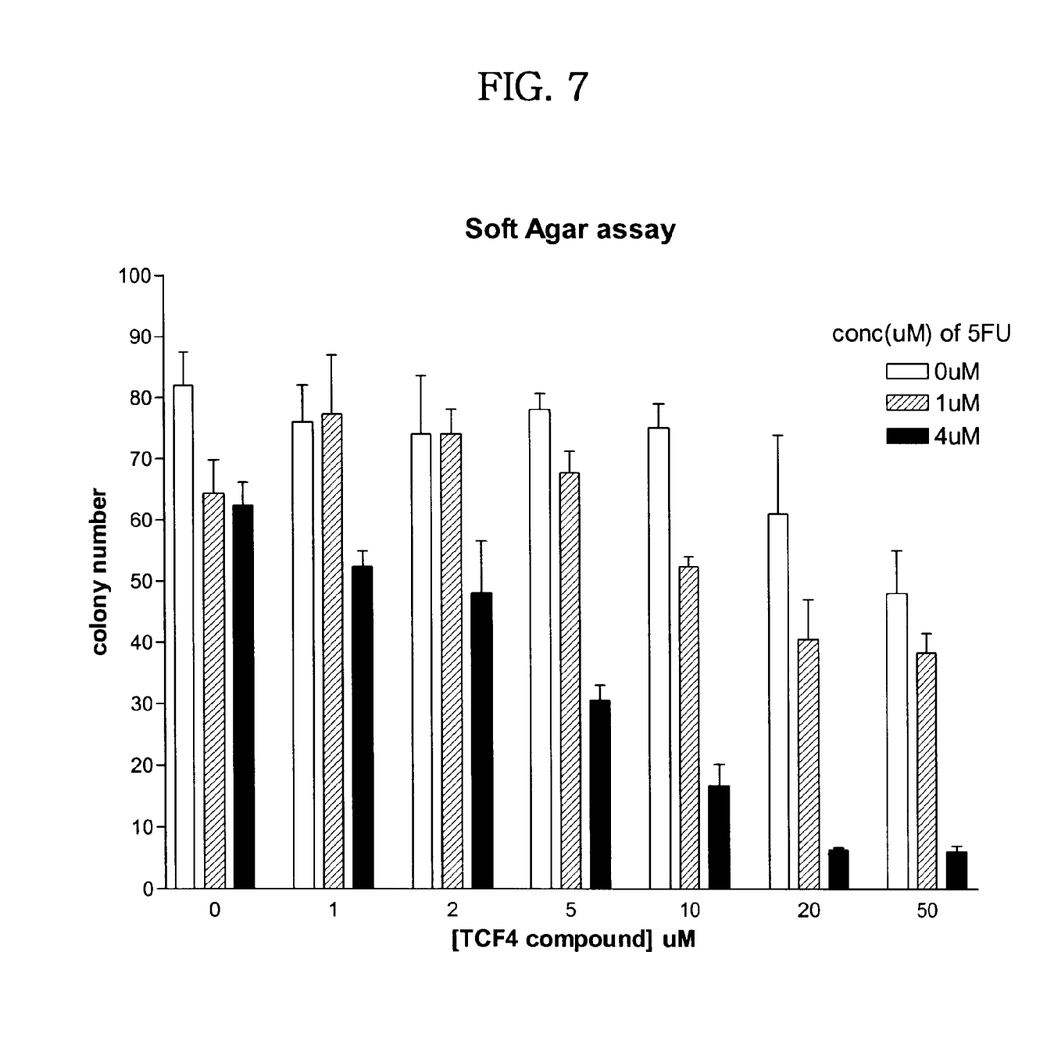
Figure 8:
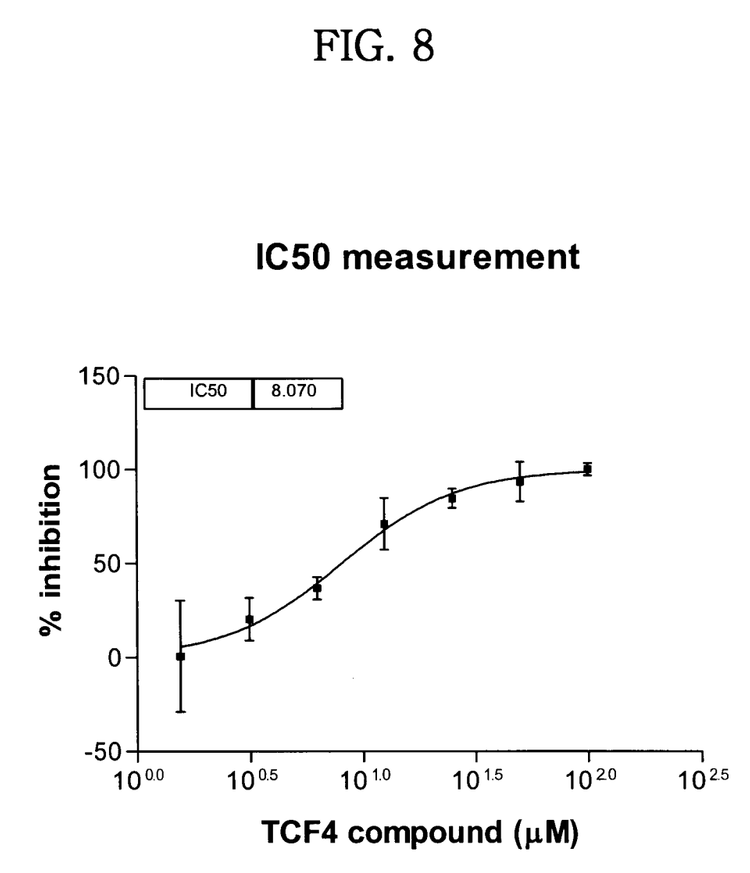
FIG. 8. Measurement of IC50 of TCF4 compound for SW480 cells. Cell growth inhibition on SW480 cells is measured at various concentrations of TCF4 compound in order to obtain the $IC_{50}$ value. Specifically, the degree of inhibition in firefly and renilla luciferase activities by TCF4 compound was determined. As a result, $IC_{50}$ of TCF compound against SW480 cell growth was found to be about 8.070 μM. Detailed procedures are the same as disclosed in Example 8.

The TCF4 Compound Inhibits Cell Growth and Colony Formation in Colorectal Cell Lines Agar plates were prepared to contain 10% FBS, 2 mM L-glutamine, 0.1 mM non-essential amino acid, 1×pen/strep and 1.6% agarose for bottom layer and DMEM containing 10% FBS, 2 mM L-glutamine, 0.1 mM non-essential amino acid, 1×pen/strep for upper layer. TCF4 compound solution and upper layer solution containing agarose were mixed and SW480 cells were added and solidified. Plates were incubated 37° C. at $CO_2$ incubator for 8 days after solidification at room temperature for 30 min and colonies were counted under microscope (FIG. 7). The results show that there is a correlation between the dose of TCF4 compound and the inhibition of cell growth and coloring formation in SW480 colorectal cell lines.

EXAMPLE 8

Bioassay for the Measurement of $IC_{50}$ of TCF Compound Against SW480 Cells

SW480 cells were transfected with the usage of Superfect™ transfect reagent (Qiagen, 301307). Cells were trypsinized briefly 1 day before transfection and plated on 6 well plate ($5 \times 10^5$ cells/well) so that they were 50–80% confluent on the day of transfection. Four microgram (TOPFlash) and one microgram (pRL-null) of DNAs were diluted in 150 μl of serum-free medium, and 30 μl of Superfect™ transfect reagent was added. The DNA-Superfect mixture was incubated at room temperature for 15 min, after that 1 ml of 10% FBS DMEM was added to this complex for an additional 3 hr of incubation. While complexes were forming, cells were washed with PBS twice without antibiotics. The DNA-Superfect™ transfect reagent complexes were applied to the cells before incubating at 37° C. at 5% $CO_2$ for 3 h. After incubation, recovery medium with 10% FBS was added to bring the final volume to 1.18 ml. After 3 hr incubation, the cells were harvested and reseeded to 96 well plate ($3 \times 10^4$ cells/well). After overnight incubation at 37° C. at 5% $CO_2$, compounds were treated for 24 hrs. Finally, the activity was checked with luciferase assay (Promega, E1960).

What is claimed is:

1. A compound having the following general formula (I):

wherein, $R_1$ is a bicyclic aryl group having 8 to 11 ring members, which may have 1 to 3 heteroatoms selected from nitrogen, oxygen or sulfur, and $R_2$ is a monocyclic aryl group having 5 to 7 ring members, which may have 1 to 2 heteroatoms selected from nitrogen, oxygen or sulfur, wherein the aryl group of $R_1$ or $R_2$ may have one or more substituents selected from a group consisting of halide, hydroxy, cyano, lower alkyl, and lower alkoxy group.

2. The compound of claim 1, wherein $R_1$ is naphthyl, quinolinyl or isoquinolinyl group, and $R_2$ is phenyl or pyridyl.

3. The compound of claim 1, wherein $R_1$ is 2-naphthyl and $R_2$ is phenyl.

4. A Pharmaceutical composition comprising the compound of claim 1 and a pharmaceutically acceptable carrier.

5. A pharmaceutical composition in which the composition comprises the compound of claim 2 and a pharmaceutically acceptable carrier.

6. A pharmaceutical composition in which the composition comprises the compound of claim 3 and a pharmaceutically acceptable carrier.

7. A method for inhibiting the growth of a tumor cell in a mammalian subject in need thereof, the method comprising administering to a tumor cell an effective amount of a compound of claim 1, wherein the tumor cell is a colorectal cell.

8. A method for inhibiting the growth of a tumor cell in a mammalian subject in need thereof, the method comprising administering to a tumor cell an effective amount of a compound of claim 2, wherein the tumor cell is a colorectal cell.

9. A method for treating a disorder modulated by Wnt signaling pathway, the method comprising administering to a subject in need thereof an effective amount of a compound of claim 1, wherein the disorder is colorectal cancer.

10. A method for treating a disorder modulated by Wnt signaling pathway, the method comprising administering to a subject in need thereof an effective amount of a compound of claim 2, wherein the disorder is colorectal cancer.

11. A method for treating a disorder modulated by TCF4-β catenin-CBP complex, the method comprising administering to a subject in need thereof an effective amount of a compound of claim 1, wherein the disorder is colorectal cancer.

12. A method for treating a disorder modulated by TCF4-β catenin-CBP complex, the method comprising administering to a subject in need thereof an effective amount of a compound of claim 2, wherein the disorder is colorectal cancer.

13. A method for inducing apoptosis in a tumor cell in a mammalian subject in need thereof, the method comprising administering to the tumor cell an effective amount of a compound of claim 1, wherein the tumor cell is a colorectal cell.

14. A method for inducing apoptosis in a tumor cell in a mammalian subject in need thereof, the method comprising administering to the tumor cell an effective amount of a compound of claim 2, wherein the tumor cell is a colorectal cell.

15. A method of treating cancer comprising administering to a subject in need thereof effective amounts of a compound of claim 1 and 5-FU, wherein the cancer is colorectal cancer.

16. A method of treating cancer comprising administering to a subject in need thereof effective amounts of a compound of claim 1 and 5-FU, wherein the cancer is colorectal cancer.

17. A method for inhibiting the growth of a tumor cell in a mammalian subject in need thereof, the method comprising administering to the tumor cell an effective amount of a compound of claim 3, wherein the tumor cell is a colorectal cell.

18. A method for treating a disorder modulated by Wnt signaling pathway, the method comprising administering to a subject in need thereof an effective amount of a compound of claim 3, wherein the disorder is colorectal cancer.

19. A method for treating a disorder modulated by TCF4-β catenin-CBP complex, the method comprising administering to a subject in need thereof an effective amount of a compound of claim 3, wherein the disorder is colorectal cancer.

20. A method for inducing apoptosis in a tumor cell in a mammalian subject in need thereof, the method comprising administering to the tumor cell an effective amount of a compound of claim 3, wherein the tumor cell is a colorectal cell.

21. A method of treating cancer comprising administering to a subject in need thereof effective amounts of a compound of claim 3 and 5-FU, wherein the cancer is colorectal cancer.

* * * * *